United States Patent [19]  
Lotz

[11] 4,316,897  
[45] Feb. 23, 1982

[54] METHOD OF LOWERING SERUM PROLACTIN

[75] Inventor: Wolfgang Lotz, Bad Krozingen, Fed. Rep. of Germany

[73] Assignee: Hoffmann-La Roche Inc., Nutley, N.J.

[21] Appl. No.: 185,812

[22] Filed: Sep. 10, 1980

[51] Int. Cl.³ .................... A61K 31/33; A61K 31/47; A61K 31/54; A61K 31/475
[52] U.S. Cl. .................................. 424/244; 424/247; 424/258; 424/262; 424/274; 424/324
[58] Field of Search ............... 424/244, 274, 247, 258, 424/262, 324

[56] References Cited

U.S. PATENT DOCUMENTS 3,864,486  2/1975  Blum .................................. 424/244

FOREIGN PATENT DOCUMENTS 6834M   11/1967  France .
1300486 12/1972  United Kingdom .

OTHER PUBLICATIONS

Merck Index, 9th Ed. (1976) Entry 6391.
Merck Index, 9th Ed. (1976) Entry 8786.

*Primary Examiner*—Frank Cacciapaglia, Jr.
*Attorney, Agent, or Firm*—Jon S. Saxe; Bernard S. Leon; Frank P. Hoffman

[57] ABSTRACT

Benzodiazepine derivatives which have tranquillizing activity, especially 1,4-benzodiazepine derivatives, can lower the serum prolactin concentration. They can reduce, dosage-dependently, the increase in the serum prolactin concentration induced by the administration of neuroleptics, which can lead to undesirable side-effects, when about 0.01 to 100 parts by weight of benzodiazepine derivatives are administered per part by weight of neuroleptic, it being immaterial whether the benzodiazepine derivative is administered before or after the neuroleptic or simultaneously therewith. The simultaneous administration of the active substances can be carried out as an ad hoc combination or in the form of a pharmaceutical combination.

5 Claims, No Drawings

METHOD OF LOWERING SERUM PROLACTIN

DESCRIPTION OF THE INVENTION

The present invention is concerned with a novel therapeutic use of benzodiazepine derivatives which have tranquilizing activity, namely the use of benzodiazepine derivatives, which can be used as minor tranquilizers, in lowering the serum prolactin concentration. Thus, it has been shown that benzodiazepine derivatives, which can be used as minor tranquilizers, can not only lower the circulating serum prolactin concentration, but in particular can also reduce dosage-dependently the increase in this hormone concentration induced by the administration of neuroleptics.

It is known that increased serum prolactin concentration can lead to undesirable side-effects such as, for example, amenorrhoea, galactorrhoea and gynaecomastia. Because of their activity in inhibiting the prolactin release, the benzodiazepine derivatives aforesaid can be combined with various neuroleptics such as tricyclics, especially phenothiazine derivatives (e.g. chlorpromazine or methopromazine), Rauwolfia alkaloids (e.g. reserpine), quinolizidine or indole derivatives (e.g. tetrabenazine or benzindopyrine), benzamides (e.g. sulpiride or metoclopramide) butyrophenones (e.g. haloperidol) and the like.

Suitable well known benzodiazepine derivatives for the purpose of the present invention are 1,4-benzodiazepine derivatives such as 7-chloro-2-methylamino-5-phenyl-3H-1,4-benzodiazepine-4-oxide (chlordiazepoxide), 7-chloro-1,3-dihydro-1-methyl-5-phenyl-2H-1,4-benzodiazepin-2-one (diazepam), 1,3-dihydro-7-nitro-5-phenyl-2H-1,4-benzodiazepin-2-one (nitrazepam), 5-(o-fluorophenyl)-1,3-dihydro-1-methyl-7-nitro-2H-1,4-benzodiazepin-2-one (flunitrazepam), 5-(o-chlorophenyl)-1,3-dihydro-7-nitro-2H-1,4-benzodiazepin-2-one (clonazepam), 7-chloro-1,3-dihydro-1-(2-diethylaminoethyl)-5-(o-fluorophenyl)-2H-1,4-benzodiazepin-2-one (flurazepam), 7-chloro-2,3-dihydro-1-methyl-5-phenyl-1H-1,4-benzodiazepine (medazepam), 7-bromo-1,3-dihydro-5-(2-pyridyl)-2H-1,4-benzodiazepin-2-one (bromazepam), 7-chloro-5-(o-chlorophenyl)-1,3-dihydro-3-hydroxy-2H-1,4-benzodiazepin-2-one (lorazepam), 7-chloro-1,3-dihydro-3-hydroxy-5-phenyl-2H-1,4-benzodiazepin-2-one (oxazepam), 7-chloro-1-cyclopropylmethyl-1,3-dihydro-5-phenyl-2H-1,4-benzodiazepin-2-one (prazepam), 7-chloro-1,3-dihydro-3-hydroxy-1-methyl-5-phenyl-2H-1,4-benzodiazepin-2-one (temazepam), derivatives containing a further ring such as, for example, 10-chloro-11b-(o-chlorophenyl)-2,3,5,11b-tetrahydro-oxazolo[3,2-d][1,4]benzodiazepin-6-(7H)-one (cloxazolam), 10-chloro-2,3,5,11b-tetrahydro-2-methyl-11b-phenyloxazolo[3,2-d][1,4]benzodiazepin-6-(7H)-one (oxazolam), 8-chloro-6-(2-chlorophenyl)-1-methyl-4H-s-triazolo[4,3-a][1,4]benzodiazepine (triazolam) as well as their analogues. Not only the neuroleptics, but also the aforementioned benzodiazepine derivatives can, if desired, also be used in the form of pharmaceutically usable salts.

The object of the present invention is accordingly the use of a benzodiazepine derivative, which can be used as a minor tranquilizer, in lowering the serum prolactin concentration, especially in lowering the increase in the serum prolactin concentration induced by the administration of neuroleptics.

Because of the excellent compatibility and low toxicity of the aforementioned benzodiazepine derivatives, undesirable side-effects are not to be reckoned with.

In the use of the benzodiazepine derivatives in accordance with the invention the ratio of the active substances can vary within relatively wide limits. Conveniently, about 0.01 to 100 parts by weight, preferably about 0.05 to 40 parts by weight, of benzodiazepine derivative are used per part by weight of neuroleptic. It is particularly preferred to use 1 to 10 parts by weight of benzodiazepine derivative per part by weight of neuroleptic.

The usual dosage varies depending on the individual and the particular indication to be treated and can amount, for example, to 1 to 100 mg depending on the neuroleptic and to 5 to 40 mg depending on the benzodiazepine derivative per day in the case of oral administration to human beings.

In order to achieve the lowering of the serum prolactin concentration in accordance with the invention, it is immaterial whether the benzodiazepine derivative is administered before or after the neuroleptic or simultaneously therewith. If the benzodiazepine derivative is administered simultaneously with the neuroleptic, then this can be carried out by administration as an ad hoc combination or in the form of a pharmaceutical combination which contains a neuroleptic or a pharmaceutically usable salt thereof and a benzodiazepine derivative, which can be used as a minor tranquilizer, or a pharmaceutically usable salt thereof.

The weight ratio of neuroleptic to benzodiazepine derivative is the same in the pharmaceutical combination as in the ad hoc combination of the two active substances.

Pharmaceutical combinations containing a neuroleptic and a benzodiazepine derivative which can be used as a minor tranquilizer are partly novel and partly known (for example, the combinations diazepam/sulpiride and bromazepam/sulpiride). The novel combinations are likewise an object of the present invention.

Disclosure relating to a combination of bromazepam and sulpiride is found in U.S. Pat. No. 3,864,486 and that of diazepam and sulpiride found in French Pat. No. 6834M.

A further object of the present invention is accordingly a still novel pharmaceutical combination of a neuroleptic with a benzodiazepine derivative which can be used as a minor tranquilizer as well as the manufacture of such a phamaceutical combination.

The following composition can be given as an example of such a pharmaceutical combination.

A tablet containing the following ingredients is manufactured:

| | |
|---|---|
| Nitrazepam | 20.0 mg |
| Sulpiride | 12.5 mg |
| Lactose | |
| Starch | |
| Talc | ad 350 mg. |
| Magnesium stearate | |

The advantageous properties of the pharmaceutical combinations in accordance with the invention as well as the activity of the benzodiazepine derivatives which can be used as minor tranquilizers in inhibiting the prolactin release should become evident on the basis of the following tests.

Male rats are accustomed for 4 days to oral treatment with a metal tube by the administration of in each case 0.2 ml of physiological sodium chloride solution. The test substances are suspended in 0.2 ml of a "Standard Suspending Vehicle" (SSV) consisting of 0.5% carboxymethylcellulose, 0.4% Tween 80 (polyoxyethylenesorbitan fatty acid ester), 0.9% benzyl alcohol and 0.9% sodium chloride in water and administered with the same metal tube in accordance with the timing schedule which is given in Tables 1 and 2 hereinafter. At the given time the animals are decapitated with the avoidance of stress, which leads to unspecific increases in the serum prolactin concentrations. Blood is collected from the body and the serum obtained therefrom is deep-frozen until the hormone determination. The prolactin concentrations are determined using a specific radioimmunoassay. The results are expressed in (ng/ml). The statistical analyses are carried out with a distribution-independent test (Kolmogorov-Smirnov test) and in several cases also with the Student t-test. The values given in the following Tables represent average values with simultaneous data for the errors from average values (Standard Error of the Mean; SEM)

TABLE 1

| Active substance p.o. (mg/kg) | | | Serum prolactin concentr. (ng/ml) | | |
|---|---|---|---|---|---|
| 0 min | 15 min | n | 30 min | P = * | P < ** |
| SSV | SSV | 13 | 17 ± 4 | | |
| Sulpiride (1) | SSV | 11 | 92 ± 11 | | |
| Sulpiride (1) | Nitrazepam (10) | 12 | 47 ± 6 | 0.0002 | 0.001 |
| 0 min | 15 min | | 60 min | | |
| SSV | SSV | 12 | 13 ± 2 | | |
| Sulpiride (1) | SSV | 12 | 50 ± 7 | | |
| Sulpiride (1) | Nitrazepam (10) | 12 | 22 ± 2 | 0.008 | 0.001 |
| 0 min | 30 min | | 45 min | | |
| SSV | SSV | 14 | 17 ± 3 | | |
| Nitrazepam(10) | SSV | 14 | 5 ± 0.2 | 0.0000 | 0.001 |
| SSV | Sulpiride (1) | 14 | 121 ± 12 | | |
| Nitrazepam(10) | Sulpiride (1) | 14 | 9 ± 2 | 0.0000 | 0.001 |
| Flunitrazepam (10) | Sulpiride (1) | 7 | 15 ± 5 | 0.0000 | 0.001 |
| Chlordiazepoxide (10) | Sulpiride (1) | 7 | 45 ± 9 | 0.0034 | 0.001 |
| SSV | Haloperidol (1) | 7 | 73 ± 14 | | |
| Nitrazepam (10) | Haloperidol (1) | 7 | 4 ± 0.3 | 0.0006 | 0.001 |
| SSV | SSV | 7 | 18 ± 5 | | |
| Medazepam (100) | SSV | 7 | 5 ± 0.3 | 0.0082 | 0.05 |
| SSV | Sulpiride (1) | 7 | 127 ± 8 | | |
| Medazepam (1) | Sulpiride (1) | 7 | 138 ± 15 | n.s. | n.s. |
| Medazepam (10) | Sulpiride (1) | 7 | 29 ± 8 | 0.0012 | 0.001 |
| Madazepam (100) | Sulpiride (1) | 7 | 17 ± 4 | 0.0012 | 0.001 |

*Kolmogorov-Smirnov test
**Student t-test
n.s. = not statistically significant
SSV = Standard Suspending Vehicle

TABLE 2

| Active substance p.o. (mg/kg) 0 min | n | Serum prolactin concentr. (ng/ml) 30 min | P = * | P < ** |
|---|---|---|---|---|
| SSV | 7 | 6 ± 1 | | |
| Haloperidol (1) | 7 | 73 ± 14 | | |
| Haloperidol (1) + Nitrazepam (10) | 7 | 23 ± 5 | n.s. | 0.01 |
| Chlorpromazine (20) | 7 | 54 ± 10 | | |
| Chlorpromazine (20) + Nitrazepam(10) | 7 | 32 ± 7 | n.s. | 0.05 |
| SSV | 7 | 15 ± 2 | | |
| Nitrazepam (0.1) | 7 | 16 ± 5 | n.s. | — |
| Nitrazepam (1) | 7 | 10 ± 1 | n.s. | — |
| Sulpiride (1) | 10 | 146 ± 11 | | |
| Sulpiride (1) + Nitrazepam (0.1) | 7 | 172 ± 12 | n.s. | — |
| Sulpiride (1) + Nitrazepam (1) | 7 | 75 ± 7 | 0.0150 | — |
| Sulpiride (1) + Nitrazepam (10) | 7 | 48 ± 11 | 0.0001 | — |
| SSV | 13 | 19 ± 3 | | |
| Sulpiride (1) | 18 | 203 ± 20 | | |
| Sulpiride (1) + Diazepam (0.01) | 7 | 231 ± 20 | n.s. | — |
| Sulpiride (1) + Diazepam (0.1) | 7 | 211 ± 21 | n.s. | — |
| Sulpiride (1) + Diazepam (1) | 14 | 224 ± 17 | n.s. | — |
| Sulpiride (1) + Diazepam (10) | 12 | 87 ± 11 | 0.0002 | — |
| Sulpiride (1) + Chlord. (0.01) | 7 | 187 ± 24 | n.s. | — |
| Sulpiride (1) + Chlord. (0.1) | 7 | 202 ± 14 | n.s. | — |
| Sulpiride (1) + Chlord. (1) | 14 | 132 ± 12 | 0.022 | — |
| Sulpiride (1) + Chlord. (10) | 11 | 97 ± 17 | 0.097 | — |
| SSV | 7 | 13 ± 2 | | — |
| Haloperidol (1) | 7 | 312 ± 80 | | — |
| Haloperidol (1) + Diazepam (10) | 7 | 17 ± 2 | | 0.01 |
| Thioridazine (10) | 7 | 131 ± 52 | | |
| Thioridazine (10) + Diazepam (10) | 7 | 17 ± 1 | 0.05 | |
| Metoclopramide (1) | 7 | 297 ± 151 | — | |

TABLE 2-continued

| Active substance p.o. (mg/kg) 0 min | n | Serum prolactin concentr. (ng/ml) 30 min | P = * | P < ** |
|---|---|---|---|---|
| Metoclopramide (1) + Diazepam (10) | 7 | 54 ± 12 | 0.05 | |
| Reserpine (1) | 7 | 69 ± 11 | — | |
| Reserpine (1) + Diazepam (10) | 7 | 20 ± 5 | 0.01 | |
| SSV | 7 | 15 ± 2 | — | |
| Sulpiride (1) | 7 | 499 ± 81 | — | |
| Sulpiride (1) + Temesta (10) | 7 | 298 ± 19 | 0.05 | |
| Sulpiride (1) + Triazolam (10) | 7 | 135 ± 39 | 0.01 | |
| Sulpiride (1) + Bromazepam (10) | 7 | 62 ± 16 | 0.001 | |

*Kolmogorov-Smirnov test; n.s. = not statistically significant
**Student t-test SSV = Standard Suspending Vehicle Female rats are given 1 or 10 mg/kg of the test substance in 0.2 ml of SSV for 10 days by the oral route. 30 minutes after the last administration the animals are decapitated with the avoidance of stress and the serum prolactin concentration is determined as described earlier.

TABLE 3

| Benzodiazepine derivative (mg/kg) | n | Prolactin (ng/ml) | P = * |
|---|---|---|---|
| SSV | 9 | 32 ± 8 | — |
| Chlordiazepoxide (1) | 5 | 30 + 13 | n.s. |
| Chlordiazepoxide (10) | 5 | 15 ± 4 | n.s. |
| Diazepam (1) | 5 | 21 ± 5 | n.s. |
| Diazepam (10) | 5 | 7 ± 0.9 | 0.003 |
| Nitrazepam (1) | 5 | 11 ± 2 | n.s. |
| Nitrazepam (10) | 5 | 4 ± 0.3 | 0.003 |
| Bromazepam (1) | 5 | 13 ± 3 | n.s. |
| Bromazepam (10) | 5 | 6 ± 1 | 0.001 |
| Clonazepam (1) | 5 | 7 ± 1 | 0.001 |
| Flunitrazepam (1) | 5 | 9 ± 1 | 0.01 |
| Flunitrazepam (10) | 5 | 7 ± 0.8 | 0.001 |

*Kolmogorov-Smirnov test
n.s. = not statistically significant
SSV = Standard Suspending Vehicle The foregoing results ascertained in the animal test can be confirmed in the clinical test described hereinafter.

6 male volunteers, who had been provided with information concerning all procedures and possible complications of the test and who had given their consent thereto, were subjected before the experiment to a thorough examination including determination of the haematological status as well as biochemical analysis of blood and urine. 30 minutes before the test an arm cannula was placed in the arm vein of each volunteer. 30 minutes later blood was removed for the determination of the basal prolactin concentration. At time 0 sulpiride was administered i.m. and placebo was administered orally. A venous blood sample was removed in each case after 15, 30, 60, 90, 120, 180, and 240 minutes. On the next day the same experiment was repeated on the same volunteers, but the oral placebo administration was replaced by 20 mg of nitrazepam. Using the combination of 6.25 mg of sulpiride i.m. and 20 mg of nitrazepam p.o. as an example, the results compiled in Table 4 are obtained.

TABLE 4

| | Serum prolactin concentration | |
|---|---|---|
| Time | 6.25 mg sulpiride i.m. | 6.25 mg sulpiride i.m. + 20 mg nitrazepam p.o. |
| −30' | 10.0 ± 1.2 | 16.1 ± 2.4 |
| 15' | 52.2 ± 4.2 | 30.0 ± 4.5 |
| 30' | 50.5 ± 1.9 | 36.0 ± 5.2 |
| 60' | 46.4 ± 4.0 | 29.7 ± 4.8 |
| 90' | 39.7 ± 1.9 | 26.5 ± 3.2 |
| 120' | 36.4 ± 4.8 | 23.8 ± 3.9 |
| 180' | 28.2 ± 4.2 | 24.8 ± 3.6 |
| 240' | 23.0 ± 3.8 | 20.3 ± 2.8 |

As will be seen from Table 4, 6.25 mg of sulpiride i.m. increases the serum prolactin concentration of 10±1.2 on average at −30 minutes to 52.2±4.2 ng/ml 15 minutes after administration of the sulpiride. The simultaneous oral administration of 20 mg of nitrazepam p.o. lowers the prolactin release to such an extent that the average concentration of 16.1±2.4 at −30 minutes only rises to 30±4.5 ng/ml 15 minutes after the sulpiride administration.

In accordance with the invention, not only the neuroleptic but also the benzodiazepine derivative is generally administered orally. The same is also true, of course, for the combinations in accordance with the invention which can be administered, for example in the form of tablets, coated tablets, dragees, hard and soft gelatin capsules, solutions, emulsions or suspensions. The administration can, however, also be carried out rectally (e.g. in the form of suppositories), locally or percutaneously (e.g. in the form of salves, creams, gels, solutions) or parenterally (e.g. in the form of injection solutions).

For the manufacture of tablets, coated tablets, dragees and hard gelatin capsules, the active substances can be processed with pharmaceutically inert, inorganic or organic excipients. Examples of such excipients which can be used for tablets, dragees and hard gelatin capsules are lactose, maize starch or derivatives thereof, talc, steric acid or its salts etc.

Suitable excipients for the manufacture of soft gelatin capsules are, for example, vegetable oils, waxes, fats, semi-solid or liquid polyols etc. However, depending on the nature of the active substances no excipients are generally required in the case of soft gelatin capsules.

Suitable excipients for the manufacture of solutions and syrups are, for example, water, polyols, saccharose, invert sugar, glucose and the like.

Suitable excipients for the manufacture of injection solutions are, for example, water, alcohols, polyols, glycerine, vegetable oils etc.

Suitable excipients for the manufacture of suppositories and local or percutaneous administration forms are, for example, natural or hardened oils, waxes, fats, semi-liquid or liquid polyols and the like.

The pharmaceutical preparations can also contain preserving agents, solubilising agents, stabilising agents, wetting agents, emulsifying agents, sweetening agents, colouring agents, flavouring agents, salts for the variation of the osmotic pressure, buffers, coating agents or antioxidants. They can also contain still other therapeutically valuable substances.

What is claimed is:

1. A method of treatment for individuals having a high prolactin concentration induced by the administration of a neuroleptic selected from the group consisting of chlorpromazine, methopromazine, reserpine, tetrabenazine, benzindopyrine, sulpiride, metoclopramide, haloperidol and thioridazine which comprises the administration of a prolactin lowering amount of a benzodiazepine derivative selected from the group consisting of chlordiazepoxide, diazepam, flunitrazepam, clonazepam, flurazepam, medazepam, bromazepam, lorazepam, oxazepam, prazepam, temazepam, cloxazolam, oxazolam and triazolam to such individual.

2. The method of claim 1 wherein the 1,4-benzodiazepine derivative is nitrazepam.

3. The method of claim 1 wherein the neuroleptic is sulpiride or haloperidol.

4. The method of claim 1 wherein about 0.01 to 100 parts by weight of benzodiazepine derivative are used per part by weight of neuroleptic.

5. The method of claim 4 wherein 0.05 to 40 parts by weight of benzodiazepine derivative are used per part by weight of neuroleptic.

* * * * *